United States Patent [19]

Grünenfelder

[11] Patent Number: 4,602,906
[45] Date of Patent: Jul. 29, 1986

[54] DENTAL INSTRUMENT FOR APPLYING POWDERED POLYMERS

[75] Inventor: Robert Grünenfelder, Vaduz, Liechtenstein

[73] Assignee: Etablissement Dentaire Ivoclar, Schaan, Liechtenstein

[21] Appl. No.: 606,793

[22] Filed: May 3, 1984

[30] Foreign Application Priority Data

May 3, 1983 [DE] Fed. Rep. of Germany ....... 3316130

[51] Int. Cl.[4] ............................................. A61C 19/02
[52] U.S. Cl. ..................................... 433/80; 137/607
[58] Field of Search ............... 433/80, 84; 137/607

[56] References Cited

U.S. PATENT DOCUMENTS 3,277,921 10/1966 Cornelius .......................... 137/607
3,500,750 3/1970 Vohl .................................. 137/607
3,874,083 4/1975 Buckley ............................... 433/80

Primary Examiner—Robert Peshock
Attorney, Agent, or Firm—Sprung Horn Kramer & Woods

[57] ABSTRACT

A dental instrument for applying powdered polymers has a reservoir for the powdered polymer that is pressurized at least while the polymer is being applied and communicates with a polymer nozzle through a line for conveying the powdered polymer, which contains a polymer-blocking mechanism. A line for conveying liquid monomer connects a liquid-monomer container, which is also pressurized, with a liquid-monomer nozzle. The release of liquid monomer is controlled by another blocking mechanism. The nozzles are positioned at an interval while being aimed at the same operating area.

14 Claims, 2 Drawing Figures

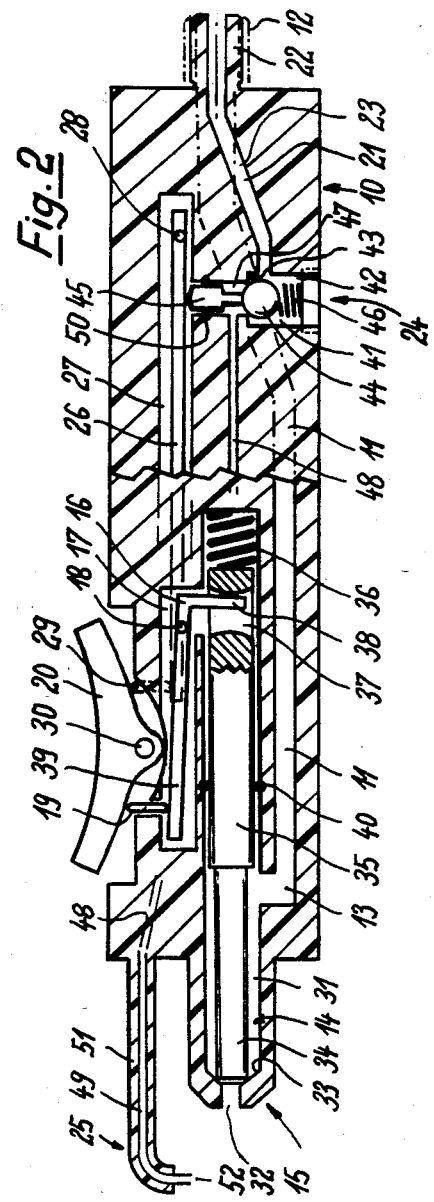
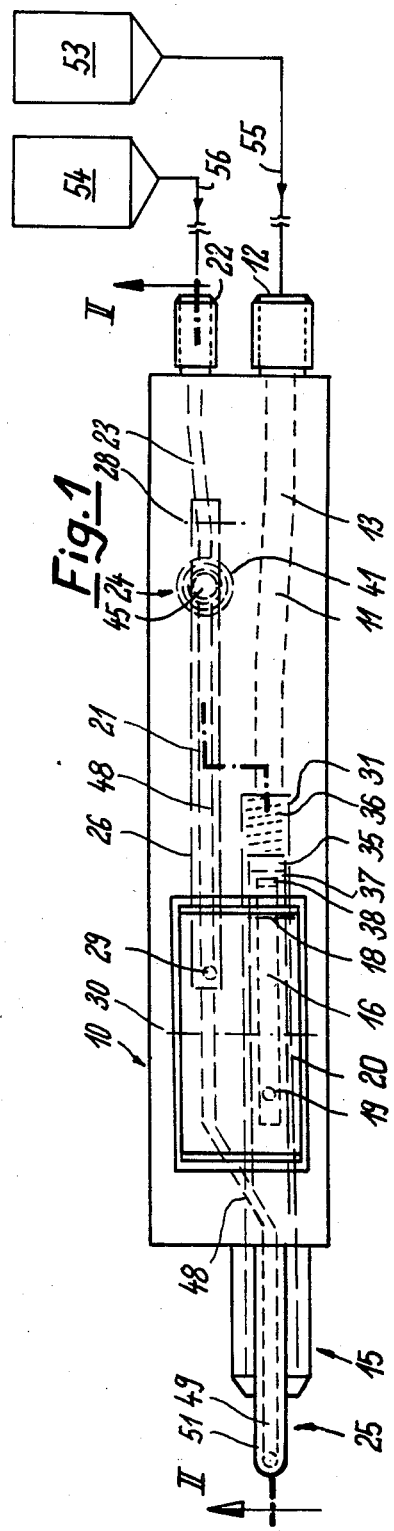

DENTAL INSTRUMENT FOR APPLYING POWDERED POLYMERS

BACKGROUND OF THE INVENTION

1. Field of the Invention

The present invention relates to a dental instrument for applying powdered polymers, with a reservoir and nozzle for the powdered polymer.

2. Discussion of Prior Art

The technique of sprinkling is essentially employed in dentistry, especially orthodontics, to create orthodontic devices. The model is wetted from a dropping flask or with a pipette at the sites at which plastic is to be applied and the plastic subsequently applied from a sprinkling bottle. The sprinkled-on polymer is then wetted again with monomer. For this a special plastic that does not tend to flow off when made into a paste is necessary, which, however, is not the case with normal autopolymers. When creating jaw-correcting devices, the dentist takes an impression of the bite for which the teeth are to be brought into the correct position and makes a plaster model from the impression. Wire elements are then fixed to the buccal side of the insulated model. An expansion screw is likewise attached in position to the model. Powdered polymer is applied from a plastic bottle with a fine spout from the palatinal or lingual tooth surface toward the middle and then wetted with monomer, also from a spray bottle with a very fine spout. These measures are repeated until the plate assumes its desired shape and strength with all retaining and motion elements. The plaster model is then placed with the modeled plate and steel elements in a pressure-polymerization device and polymerized. Finally, the polymerized plate is conventionally polished and inserted in the patients mouth by the dentist. A force is exerted on the wires by adjusting the expansion screw that is accordingly transmitted to the teeth that are to be corrected. This method of creating a plastic is difficult and time-consuming because the dentist or dental technician must constantly alternate between picking up and putting down the plastic bottle with the powdered polymer and the spray bottle with the liquid monomer and because a great deal of care must be devoted to applying the right amount in each case. Constantly changing the bottles makes it difficult to concentrate on the operation.

SUMMARY OF THE INVENTION

The object of the present invention is to simplify and accelerate the application of the plastics and especially to make it possible to apply both the polymer and the monomer with greater control and precision.

This object is attained in accordance with the invention in that that the polymer reservoir is pressurized at least while the polymer is being applied and communicates with the polymer nozzle through a line for conveying the powdered polymer, which contains a polymer-blocking mechanism, in that a line for conveying liquid monomer, which contains a monomer-blocking mechanism, connects a liquid-monomer container, which is also pressurized at least while the monomer is being applied, with a liquid-monomer nozzle, and in that the nozzles are positioned at an interval while being aimed at the same operating area.

Although the instrument is especially appropriate for creating orthodontic jaw-correction devices, it can also be used whenever a a mixture of polymer and monomer is needed, as in the repair of prostheses for example.

The rates at which both the powdered polymer and liquid monomer are applied can be controlled with extraordinary precision, with extremely small amounts applied to the workpiece exactly where desired. The instrument is easy for the dentist or technician to hold, considerably reducing the necessary motions and allowing greater concentration on the operation. The materials do not come into contact with the operator's skin. Material consumption is reduced in a practical way to the minimum required. The reduction in the number of manipulations required saves time. Both blocking mechanisms are activated interrelatedly by a common rocker switch mounted on a handle that accommodates all the controls and lines. The handle and switch are designed in accordance with principles of human engineering.

DESCRIPTION OF PREFERRED EMBODIMENTS

Both blocking mechanisms and nozzles can be incorporated next to their associated line sections in one handle.

Both blocking mechanisms can be activated by a single rocker switch.

The handle or the lines inside it can communicate with the powered-polymer reservoir or the liquid-monomer container through flexible lines.

A channel and the outlet of the powdered-polymer nozzle can extend along the handle and on the side of the outlet facing the channel the powdered polymer blocking mechanism can comprise a valve seat on which a valve tappet rests in the blocking state. The valve tappet can be positioned on the free end of a valve piston that slides longitudinally inside the handle subject to a compression spring that holds the valve tappet against the valve seat in the blocking state, whereby the valve piston has a recess into which a cam extends. The cam can be activated by the rocker switch to open the powdered-polymer blocking mechanism.

The liquid-monomer nozzle can comprise a bent channel with an outlet that releases liquid monomer at an angle of 90° to the direction in which the powdered polymer is released.

The dental instrument can have a spring-loaded ball valve, which can be opened by a valve piston activated by the rocker switch, in the liquid-monomer line inside the handle.

At least the channel in the liquid-monomer line can be a capillary tube.

The channel-capillary tube can be positioned in a plastic part that, along with the channel-capillary tube, can be deformed and retains its shape and/or is interchangeable.

The liquid-monomer nozzle can have a channel with an outlet that releases liquid monomer at an acute angle to the direction in which the powdered polymer is released.

In another embodiment with a reservoir and nozzle for the powdered polymer, the polymer reservoir can be pressurized at least while the polymer is being applied and can communicate with the polymer nozzle through a line for conveying the powdered polymer, which line contains a polymer-blocking mechanism. The liquid-monomer line can connect a liquid-monomer container that is also subject to a pressure that can be varied by means of another blocking mechanism with a liquid-monomer nozzle, and the nozzles can be positioned at an interval while being aimed at the same operating area.

In this latter embodiment both blocking mechanisms and nozzles can be incorporated next to their associated line sections in one handle, both blocking mechanisms can be activated by one rocker switch, flexible lines can be provided as in the first embodiment, the powdered-polymer nozzle and the powdered-polymer blocking mechanism can be designed as in first embodiment, and in the liquid-monomer nozzle can designed and positioned as in the first embodiment.

Some preferred embodiments of the invention will now be described with reference to the attached drawings, wherein

BRIEF DESCRIPTION OF THE DRAWINGS

FIG. 1 is a top view of an instrument in accordance with the invention and

FIG. 2 is a section along the line II—II in FIG. 1.

DETAILED DESCRIPTION OF THE SPECIFIC EMBODIMENTS

The handle 10 of the illustrated embodiment is designed in accordance with principles of human engineering to fit the hand of the dentist or dental technician.

A line 11 (FIG. 2) for conveying a powdered polymer and another line 21 for conveying a liquid monomer extend longitudinally inside handle 10. Powdered-polymer line 11 extends from a connection 12 through a section 13 to a blocking mechanism 14 and ends in a powdered-polymer nozzle 15. Liquid-monomer line 21 extends from a connection 22 through a section 23 to a blocking mechanism 24 and ends in a liquid monomer nozzle 25. A powdered-polymer blocking mechanism 14 is controlled by a lever 16 that swivels on an axis 18 in a recess 17 in the housing of handle 10 and is controlled in turn by a tappet 19. Liquid monomer blocking mechanism 24 is controlled by a lever 26 that swivels on an axis 28 in a recess 27 in the housing of handle 10 and is controlled in turn by a tappet 29. Tappets 19 and 29 are activated by a single rocker switch 20 that swivels on axis 30 in the housing of handle 10.

A channel 31 extends along handle 10 from the housing of the handle into powdered-polymer nozzle 15, constituting a section of powdered-polymer line 11. The free end of channel 31 consists of an outlet 32 for applying the powdered polymer. There is a valve seat 33 upstream of powdered-polymer outlet 32 with respect to channel 31. A valve tappet 34 that is part of powder-polymer blocking mechanism 14 rests against valve seat 33 when the powdered-polymer supply is to be blocked. Valve tappet 34 is positioned on the free end of a valve piston 35 that slides longitudinally inside handle 10 subject to a compression spring 36 that holds the tappet against valve seat 33 when the powdered-polymer supply is to be blocked. Valve piston 35 has a recess 37. A cam 38 on powdered-polymer control lever 16 extends into recess 37. Lever 16 is two-armed and swivels on powdered-polymer control axis 18 with its other arm resting against powdered-polymer control tappet 19. Compression spring 36 holds powdered-polymer blocking mechanism 14 in the blocking position and powdered-polymer control tappet 19 in its rest position, in which rocker switch 20 is in a neutral state as illustrated in FIG. 2.

A sealing ring 40 is positioned around valve piston 35 in the wall of channel 31 inside handle 10, sealing off powdered-polymer line 11 or its section 13 from powdered-polymer control recess 17.

The blocking mechanism 24 in liquid-monomer line 21 is a ball valve positioned in an offset bore 41 that extends transversely at the connection end of handle 10. Bore 41 has a wider section 42 that communicates with liquid-monomer connection 22 through section 23 of liquid-monomer line 21 and has a valve seat 43 at the offset.

The ball 44 of the valve rests on valve seat 43 subject to a compression spring 46 and can be activated by a valve piston 45. Valve piston 45 can be displaced axially within a narrow section 47 of bore 41. Valve piston 45 is surrounded by a sealing ring 50 inside the housing of handle 10 that separates the space of valve 43 and 44 from the liquid-monomer control recess 27 in which the single-armed liquid-monomer control lever 26 swivels on axis 28 and engages valve piston 45. Compression spring 46 holds ball 44 against valve seat 43 when the supply of liquid monomer is to be blocked and hence holds liquid-monomer control lever 26 against tappet 29, which engages rocker switch 20 on the side of rocker-switch axis 30 opposite tappet 29, maintaining it in the rest state as illustrated in FIG. 2.

One section 48 of liquid-monomer line 21 extends from between valve seat 43 and sealing ring 50 to a channel 49 that functions as a capillary tube for the liquid monomer inside liquid-monomer nozzle 25. As will be evident from FIG. 2, channel 49 is a tube embedded in a plastic part 51 that is deformable and/or can be connected as an independent part to handle 10. It is practical for channel 49 to be bent such that the outlet 52 for the liquid monomer will extend at an angle of 90° to the outlet 32 or direction of emergence of the powdered polymer. The axes of powdered-polymer outlet 32 and liquid-monomer outlet 52 can also be at an acute angle such as an angle of 60°. Furthermore, liquid-monomer outlet 52 is displaced with respect to powdered-polymer outlet 32 or far enough away from it so that no liquid monomer can get onto powdered-polymer nozzle 15 when both are aimed at a specific area on the workpiece at any stage of the operation. Liquid-monomer nozzle 25 does not need to be positioned directly above powdered-polymer nozzle 15 but can be displace to one side of it.

The inside diameter of powdered-polymer line 11 is in the range of 1 to 10 mm and is 2 to 8 mm in practical terms. A preferred embodiment is 4 mm in diameter. The diameter of powdered-polymer outlet 32 is in the range of 1 to 5 mm and is 2.5 mm in practical terms. The inside diameter of liquid-monomer line 21 is in the range of 0.5 to 8 mm, preferably 1 to 5 mm. A practical diameter is 1 mm. The diameter of liquid-monomer outlet 52 is preferably in the range of 0.1 to 1.5 mm, especially 0.3 to 0.5 mm.

The illustrated embodiment has two special containers with a capacity of about 500 ml, one a reservoir 53 for the powdered polymer and the other a storage container 54 for the liquid monomer. Reservoir 53 communicates with powdered-polymer connection 12 through a flexible line 55 and container 54 with liquid-monomer connection 22 through a flexible line 56. An operating pressure of 0.7 bars is maintained continuously or intermittently inside the containers, which are funnel-shaped at the bottom. The pressure may vary between 0.3 and 2 bars.

At the input to powered-polymer reservoir 53 is a sieve, not illustrated, that retains particles larger than 0.8 mm. The pressure in powered-polymer reservoir 53 is just sufficient to cause the polymer to trickle out or to force it out in a fine stream, depending on the extent to which the blocking mechanism is opened, without allowing it to shoot out when the mechanism is opened. The extent to which valve tappet 34 is lifted off valve seat 33 can be precisely controlled with rocker switch 20.

Basically any polymer that is appropriate for creating orthodontic devices or repairing dental prostheses can be employed. Such materials include polyvinyl chloride, polystyrene, polyamides, epoxy compounds, and polyurethanes, or their mixed polymers. Especially preferred polymeric methacrylates are ethyl methacrylates and their copolymers. The particle size of the polymers employed ranges between 80 and 600 $\mu$m, preferably between 120 and 350 $\mu$m, especially between 150 and 250 $\mu$m. Monomers include the monomeric compounds of the aforesaid polymers as well as the mono-, di-, or polyfunctional compounds of the acrylates or methacrylates if their viscosity allows them to adapt to the iquid-monomer nozzle. Especially to be employed however is methyl methacrylate, which may also contain additives inb the form of catalysts, ultraviolet stabilizers, and di- or polyfunctional methacrylate compounds. A filter can be positioned at the output of liquid-monomer container 54 to intercept any contaminants larger than 5 $\mu$m.

When the instrument is at rest as illustrated in FIG. 2, both blocking mechanisms 14 and 24 are closed. When rocker switch 20 is activated counterclockwise, powdered-polymer control tappet 19 and hence arm 39 is forced down. Powdered-polymer control lever 16 swivels counterclockwise around axis 18, cam 38 lifts valve tappet 34 off valve seat 33 against the force of compression spring 36, and powdered polymer is released from line 11 through outlet 32 subject to precise control by means of rocker switch 20. Since liquid-monomer blocking mechanism 24 remains closed during this operation, no liquid monomer can escape through outlet 52.

When, on the other hand, rocker switch 20 is swiveled clockwise, powdered-polymer blocking mechanism 14 is closed and liquid-monomer control tappet 29 forced down by the pivoting action of single-armed lever 26. Valve piston 45 is accordingly displaced against the force of compression spring 46 toward ball 44, which is lifted from valve seat 43 so that liquid monomer can flow through liquid-monomer line section 48 into channel-capillary tube 49 and emerge through outlet 52.

Handle 10 does not have to be put down during these operations. The dental equipment that handle 10 is attached to through flexible lines 55 and 56 can have a rest for the handle incorporating a switch that discontinues the supply of pressure to containers 53 and 54 when the handle is placed on it.

In another embodiment of the invention, liquid-monomer line 21 extends all the way through handle 10 between liquid-monomer connection 22 and channel-capillary tube 49 and liquid-monomer blocking mechanism 24, which is activated by rocker switch 20, is positioned in the pressure-medium line from liquid-monomer container 54.

What is claimed is:

1. A dental instrument for applying powdered polymers comprising a handle, a reservoir for said powdered polymer, an outlet nozzle for said powdered polymer, a polymer conduit providing communication between said polymer reservoir and said polymer nozzle, means for maintaining pressure upon the contents of said polymer reservoir to force polymer to pass through said polymer line to said polymer nozzle, a reservoir for a liquid monomer, an outlet nozzle for the liquid monomer, a liquid monomer conduit providing fluid communication between the liquid monomer reservoir and the liquid monomer nozzle, means for maintaining pressure on the contents of the liquid monomer reservoir, wherein said polymer nozzle and said liquid monomer nozzle are spaced apart while being aimed at the same general operating area at different angles and blocking means disposed in the handle for normally preventing powder and liquid from passing through their respective nozzles and actuatable by a rocker switch to alternatively permit the powder to flow through the polymer nozzle while the liquid flow is blocked and to permit liquid to flow to the monomer nozzle while the powder flow is blocked.

2. A dental instrument according to claim 1, wherein said nozzles and at least a portion of each of said polymer and said liquid monomer conduits extend inside the handle.

3. A dental instrument according to claim 2, wherein at least a portion of said polymer conduit upstream of said blocking means is flexible.

4. A dental instrument according to claim 3, wherein at least a portion of said liquid monomer conduit upstream of said blocking means is flexible.

5. A dental instrument according to claim 1, wherein the blocking means includes means for blocking the polymer flow comprising a polymer channel in said handle in facing communication with the outlet of said polymer nozzle, a polymer valve seat on the side of said outlet facing said channel in which rests a polymer valve tappet of said polymer means.

6. A dental instrument according to claim 5 wherein said polymer valve tappet is positioned on the free end of a polymer valve piston and is longitudinally slideable in said handle in response to a compression spring bearing thereagainst to force said polymer valve tappet against said polymer valve seat, said polymer valve piston engageable by a cam whereby to compress said compression spring to cause said polymer valve tappet to slide longitudinally in said channel and become dislodged from said polymer valve seat, said cam activated by said rocker switch.

7. A dental instrument according to claim 1 wherein said liquid monomer nozzle has a bent channel with an outlet that releases liquid monomer at an angle of 90° to the direction in which the powdered polymer is released.

8. A dental instrument according to claim 1, wherein the blocking means includes means for blocking the monomer flow comprises a spring loaded ball valve in the monomer conduit and actuatable by said rocker switch via a liquid monomer valve piston.

9. A dental instrument according to claim 8 wherein at least a portion of said liquid monomer line downstream of said value ball is a capillary tube.

10. A dental instrument according to claim 9 wherein at least a portion of said capillary tube is disposed in a plastic deformable member which can hold a shape but can be deformed to another shape.

11. A dental instrument according to claim 1 wherein said liquid-monomer nozzle has a channel with an outlet that releases liquid monomer at an acute angle to the direction in which the powdered polymer is released.

12. In a dental instrument for applying powdered polymers, comprising a handle, a reservoir for powdered polymer and a nozzle receptive of said powdered means for pressurizing the polymer reservoir at least while the polymer is being applied comprising polymer-blocking means disposed in the handle, a liquid monomer container, a nozzle receptive of liquid from the liquid monomer container through a monomer line, wherein the nozzles are disposed at an interval while being aimed at the same operating area at different angles, means for maintaining pressure in the liquid container including a pressure line to the container and means disposed in the handle for blocking liquid monomer flow to the nozzle comprising means blocking the pressure line, wherein at least a portion of the polymer and monomer lines are disposed in the handle and at least a portion of the polymer and monomer lines upstream of the blocking means is flexible, and further comprising a rocker switch for actuating the monomer and polymer blocking means.

13. A dental instrument according to claim 12 wherein said liquid monomer nozzle has a bent channel with an outlet that releases liquid monomer at an angle of 90° to the direction in which the powdered polymer is released.

14. A dental instrument according to claim 12 wherein the liquid monomer nozzle has a channel with an outlet that releases liquid monomer at an acute angle to the direction in which the powdered polymer is released.

* * * * *